United States Patent [19]

Drago et al.

[11] Patent Number: 5,012,008

[45] Date of Patent: Apr. 30, 1991

[54] SUPPORTED AMORPHOUS PHASE HETEROGENEOUS CATALYSTS FOR BIPHASIC HYDROFORMYLATION

[76] Inventors: Russell S. Drago, 2281 NW. 24th Ave., Gainesville, Fla. 32605; Mark J. Barnes, 104 The Bunkers, Aiken, S.C. 29801; Michael J. Naughton, 7301-69 W. University Ave., Gainesville, Fla. 32607

[21] Appl. No.: 461,828

[22] Filed: Jan. 8, 1990

[51] Int. Cl.$^5$ ............................................. C07C 45/50
[52] U.S. Cl. ..................................... 568/454; 568/451; 568/452
[58] Field of Search ............... 568/451, 454, 452, 453, 568/882

[56] References Cited

U.S. PATENT DOCUMENTS

| | | | |
|---|---|---|---|
| 3,733,362 | 5/1973 | Biale | 568/454 |
| 3,855,307 | 12/1974 | Rony et al. | 568/454 |
| 4,504,684 | 3/1985 | Fox et al. | 568/454 |
| 4,537,997 | 8/1985 | Kojima et al. | 568/454 |
| 4,801,754 | 1/1989 | Bach et al. | 568/454 |

FOREIGN PATENT DOCUMENTS

| | | | |
|---|---|---|---|
| 2064471 | 7/1971 | Fed. Rep. of Germany | 568/454 |
| 3301591 | 7/1984 | Fed. Rep. of Germany | 568/454 |

*Primary Examiner*—Werren B. Lone
*Attorney, Agent, or Firm*—Depaoli & O'Brien

[57] ABSTRACT

Normal aldehydes are produced in high selectivity by the vapor phase reaction of lower olefins with hydrogen and carbon monoxide in the presence of supported liquid phase catalysts at temperatures of 80° C. to 100° C. under pressures of 1 to 5 atmospheres.

12 Claims, No Drawings

SUPPORTED AMORPHOUS PHASE HETEROGENEOUS CATALYSTS FOR BIPHASIC HYDROFORMYLATION

BACKGROUND OF THE INVENTION

1. Field of the Invention

The invention relates to the production of aldehydes and more particularly to the use of coatings on solids to effect biphasic hydroformylation, e.g., the vapor phase reaction of lower olefins with hydrogen and carbon monoxide in the presence of a liquid phase heterogeneous catalyst or a liquid phase reaction using an insoluble amorphous coating containing the catalyst on a support in contact with a second liquid phase containing a higher olefin or a solution of the olefin in a hydrophobic solvent.

2. Description of the Invention

Hydroformylation of an olefin to produce a formyl-substituted derivative of the olefin is well-known in the art as an economically attractive method for producing aldehydes which are primary intermediates in the manufacture of alkanols such as n-butanol and the corresponding alkanoic acids. Also important are such end products as 2-ethylhexanol, which is formed from n-butyraldehyde by a sequence of steps including aldoling, dehydration, and hydrogenation by methods which are well-established in the art.

While hydroformylation processes using cobalt carbonyl as the major component of the catalyst have been known and used for many years, systems in which the catalyst comprises rhodium hydrido carbonyl complexed with an organic ligand have been developed more recently and are now favored over the older technology since they can be used under relatively mild reaction conditions and can be controlled so as to yield a product in which the normal isomer of the aldehyde predominates over the branched-chain isomer to a greater extent than has normally been obtained heretofore when using the older methods. It will be understood in this regard that for most industrial purposes, including use as a raw material for production of the corresponding alkanoic acids (by catalytic oxidation of the aldehyde) and also for the production of higher molecular weight alcohol derivatives (as by aldoling, etc.), the normal aldehyde is strongly preferred over the branched-chain isomer. In the case of the butyraldehydes, for example, n-butyraldehyde finds a ready and expanding market whereas isobutyraldehyde has fewer uses and is considered an undesirable by-product. Similarly, in the case of longer-chain aldehydes such as heptaldehyde, the normal isomers can be used to produce high-quality ester-type synthetic lubricants, while the properties of the corresponding branched-chain isomers are such that they have lesser value for such purposes.

Use of the rhodium-containing catalyst systems results in the attainment of an improved normal:iso ratio in the aldehyde products formed in these processes (as compared with the cobalt-based systems), but formation of the branched-chain isomer continues to be a significant economic drawback. By controlling such parameters as carbon monoxide partial pressure, carbon monoxide:hydrogen ratio, etc., it is possible to influence the product distribution somewhat in a favorable direction. A very significant process parameter is also the ratio of ligand to rhodium in the catalyst mixture, it having been discovered that the normal:iso ratio in the product increases with increasing ligand:rhodium ratio. For example, phosphine-type ligands, such as triphenylphosphine, are customarily employed in rhodium-catalyzed hydroformylation systems in proportions such that the ratio of phosphorus to rhodium is at least about 10:1, ranging on upwardly to as much as 1000:1. Ratios lower than about 2:1 have been found to be unsatisfactory. As the phosphorus:rhodium ratio is increased in the systems employing the previously-recognized ligands such as triphenylphosphine, there is a gradual improvement in the normal:iso ratio in the product aldehydes indicative of an equilibrium-type reaction. Thus, normal practice is to use a substantial excess of ligand on the basis of judgement and of the rapidity of catalyst deactivation observed with various ligand:rhodium ratios.

In the prior art processes for hydroformylation of olefins with hydrogen and carbon monoxide, the typical catalysts employed are homogeneous and are dissolved in the liquid phase reaction system to achieve a high rate of reaction and selectivity. For high boiling alkenes (greater than $C_5$), systems of this type, however, suffer the disadvantage of product separation, catalyst recovery and catalyst regeneration. Liquid phase systems, for example, require additional processing steps and special equipment for separation of dissolved metal catalysts from liquid reaction products, thereby contributing to significant catalyst losses due to handling of catalyst solutions.

In attempts to overcome the inherent disadvantages in the use of homogeneous catalysts, it has been proposed in U.S. Pat. No. 3,733,362 to use heterogeneous catalysts comprising a Group VIII metal and a biphyllic ligand impregnated on an inert solid support such as silica, alumina, silica-alumina, titania, etc., activated carbon, charcoal, graphite, clays, naturally occurring aluminosilicates such as mordenite, chabazite and gmelinite, and synthetic zeolites such as zeolites X, Y, L or J. It has also been proposed to use a solid catalyst comprising a solid inorganic support material and a solid, active catalytic material comprising a polymeric transition metal complex, e.g., rhodium, for the hydroformylation of olefins to produce aldehydes, as disclosed in U.S. Pat. No. 4,504,684. It has been further proposed in U.S. Pat. No. 3,855,307 to Rony et al to use the combination of liquid and solid phase catalysts in a single unitary multiphase catalytic entity in which a liquid phase catalyst is disposed upon porous supports or substrates. The liquid phase catalyst, which is liquid under reaction conditions, comprises a non-volatile and more volatile solvent with a catalytic component such as a metal salt dissolved or dispersed therein. Rony et al reported maximum selectivities to the linear aldehyde (n-butyraldehyde) of 10:1 using supported rhodium and cobalt based metal complexes in a liquid phase of a non-volatile liquid such as butyl benzyl phthalate, diphenyl ether and diphenyl 2-ethylhexyl diphenyl phosphate. See, also, Rony & Roth, J. Molecular Catalysis 1 (1975/76)13. Insoluble heterogeneous hydroformylation catalysts for converting propylene to butyraldehyde have also been proposed by Hjortkjaer et al, J. Molecular Catalysis 6 (1979)405 who supported hydridiocarbonyltris(triphenylphosphine) rhodium I and excess triphenylphosphine on various supports for the hydroformylation of propene at 100° C. under a pressure of 11 atmospheres. Gerritsen et al, J. Molecular Catalysis 9 (1980), pages 139 and 241, further disclose heterogeneous hydroformylation of ethylene and propylene with supported rhodium complexes of the above type dissolved in triphenylphosphine at reaction conditions of 100° C. and 80 psig. Selectivities to the normal isomer, however, were 10:1 with one example yielding a 20:1 normal:iso ratio.

While supported liquid phase catalysts offer a number of advantages over homogeneous hydroformylation processes of the prior art, including product recovery catalyst recycle and catalyst regeneration, they also suffer the disadvantage of low product selectivities of 95%, or less, to the desired linear aldehyde product.

SUMMARY OF THE INVENTION

In accordance with the invention, it has been discovered that supported amorphous phase heterogeneous catalysts are unique catalysts for the hydroformylation of olefins under biphasic conditions by reaction with hydrogen and carbon monoxide under critical conditions of temperature and pressure. Such catalysts are known materials and are characterized as comprising a complex containing a Group VIII metal complex dispersed in a non-volatile film containing dissolved triphenylphosphine which is supported on a porous solid support. The amorphous (non-crystalline) phase can be a non-volatile liquid or amorphous (preferably rubbery) polymer which forms a coating on the solid support that prevents loss of said coating to the vapor or liquid phase reactant. By means of the present invention, supported amorphous phase catalysts provide the activity and selectivity advantages of homogeneous systems with the further advantages of product separation, catalyst recovery, catalyst regeneration and catalyst recycle that is obtained with heterogeneous catalysts.

DETAILED DESCRIPTION OF THE INVENTION

A complete and thorough description of the supported amorphous phase heterogeneous catalyst (SAPC) used for purposes of the invention is described in U.S. Pat. No. 3,855,307 to Rony et al, hereby incorporated by reference. The scope of useful catalyst compositions which thus may be employed in the present invention is identical to the scope of catalyst compositions set forth in the Rony et al reference except that the amorphous phase must dissolve triphenylphosphine to provide an excess of this reagent in the reaction medium.

Surprisingly, and unexpectedly, it has been found that hydroformylation of olefins in the vapor phase with a supported liquid phase catalyst provides an unusually high selectivity to the normal aldehyde product when the temperature is within the range of 80° C. to 100° C. at a pressure of 1 to 5 atmospheres, preferably 1 to 3 atmospheres. With lower molecular weight olefins such as propylene, product selectivities to the linear isomer have been obtained during hydroformylation which exceed greater than 99% n-butyraldehyde.

The hydroformylation of an olefinic feedstock, e.g., an alkene, by the process of the invention is effected by introducing the olefin to be hydroformylated as a vapor or gas stream along with a gaseous mixture of hydrogen and carbon monoxide into a conventional catalytic reactor which contains the supported amorphous phase catalyst (SAPC) in the form of packed towers or as trays of catalyst, with conventional feed and discharge means for gaseous reactants and separation and recovery of the aldehyde product from any unreacted gases.

The (SAPC) catalyst may be used in the form of a fixed or fluidized bed, with or without inert filler material. Generally, any of the known procedures heretofore employed in vapor phase heterogeneous catalysis may be employed for working up the reaction mixture. The product gas stream, for example, may be passed through separation means for recovery of aldehyde product while unreacted olefin, carbon monoxide and hydrocarbon are recycled to the reaction zone. Alternatively, a biphasic system can be created, for example, by employing a hydrophilic liquid or polymer amorphous phase containing the catalyst in contact with the liquid alkene or a solution of the alkene in a hydrophobic solvent. Batch or countercurrent flow reactors could be employed.

The olefinically-unsaturated feedstock which is to be hydroformylated by the present improved process can be any of the many types of olefin already known in the art to be suitable for rhodium-catalyzed hydroformylations, especially olefinic compounds having in the molecule from 2 up to about 20 carbon atoms. Although mono-unsaturated compounds are normally employed and of particular practical importance, di- and triethylenically unsaturated olefins can also be used, the product in each case being, if complete hydroformylation is carried out, a derivative having up to one additional carbon atom for each double bond in the parent compound. Olefinic compounds having substituted groups, e.g., ethyleneically-unsaturated alcohols, aldehydes, ketones, esters, carboxylic acids, acetals, ketals, nitriles, amines, etc., can be hydroformylated as well as the simple mono-alkenes which are particularly useful and of particular commercial importance. Broadly, ethylenically-unsaturated compounds which are free of atoms other than carbon, hydrogen, oxygen, and nitrogen are readily hydroformylated, and more particularly compounds consisting solely of oxygen, hydrogen, and carbon. Some specific classes of substituted olefins to which the hydroformylation process is applicable are: unsaturated aldehydes such as acrolein and crotonaldehyde; alkanoic acids such as acrylic acid; and unsaturated acetals, such as acrolein acetal. More commonly, suitable hydroformylation feedstocks include the simple alkenes such as ethylene, propylene, the butylenes, etc.; alkadienes such as butadiene and 1,5-hexadiene; and the aryl and alkaryl derivatives of the foregoing. Lower mono-alkenes of 2 to about 12 carbon atoms are especially useful, especially alpha olefins such as propylene, butene-1, pentene-1, hexene-1, cyclohexene, hexyne-1, heptene-1, octene 1, nonene-1, decene-1 and dodecene-1 and their isomers.

Preferred olefinic feedstocks for a biphasic system using a vapor feed of reactants are olefins having from 2 to 6 carbon atoms, including monolefins and diolefins such as ethylene, propylene, butene-1, pentene-1, pentene-2, butadiene, pentadiene, hexene-1, cyclohexene and the like. For a biphasic system employing a liquid feed, higher molecular weight olefins are preferred.

The hydroformylation process is conducted under a total reaction pressure of hydrogen and carbon monoxide combined of about 1 atmosphere, or even less, up to a combined pressure of 5 atmospheres at a reaction temperature of 80° C. to 100° C. One atmosphere of pressure corresponds to 15 psi whereas 5 atmospheres corresponds to about 75 psi, the term "psi" referring to pounds per square inch. At pressures of more than 5 atmospheres (75 psi), conversion is increased but selectivity to the normal aldehyde decreases rapidly. Typically, within the recited temperature and pressure ranges and using propylene as the olefin feedstock, the selectivity to normal aldehyde is greater than 98% at 1 atmosphere pressure and 95% selectivity at 5 atmospheres.

The hydroformylation reaction is conducted at a temperature of 80° C. to 100° C. with a temperature of 80° C. to 90° C. being preferred. At temperatures of 125° C., catalyst decomposition occurs whereas at temperatures below 80° C., e.g., 75° C., selectivity is decreased.

The ratio of hydrogen to carbon monoxide to alkene in the reaction vessel may be varied over wide ratios to influence conversion of alkenes and selectivity to the normal aldehyde product as desired. The ratio of hydrogen to carbon monoxide in the reaction vessel may range from about 10:1 to 1:10 and can be extended to about 50:1 to 1:50. Usually, the ratio of hydrogen to carbon monoxide will be within the range of about 6:1 to 1:6, preferably about 1:1. At least one mole of hydrogen and carbon monoxide should be supplied for each mole of olefin reacted. At mole ratios of 1:1:1, 1:1:0.1 or 1:1:2 ($H_2CO$:alkene), selectivities of greater than 98% to the linear isomer (n-butyraldehyde) have been obtained. Increasing the mole ratio of alkene generally increases selectivity at the expense of conversion.

The gas mixture, including olefin, is conducted over the catalyst at a gas hourly space velocity of 500 to 10,000 gas volumes per catalyst volume per hour, and preferably about 1,000 to 5,000 gas volumes per hour. In the examples set forth hereinafter, the weight hourly space velocity was within the range of 2.44 to 1.63 per hour.

The biphasic conditions employed in most of the screening involved gas phase reactants in contact with the (SAPC) catalyst because these are more stringent conditions than the (SAPC) catalyst in contact with liquid phase reactants. Greater concentration of alkene in the SAPC is expected when in contact with a liquid phase alkene. Extension of the SAPC catalyst to biphasic liquid alkenes is encompassed in the embodiment of the claims.

The (SAPC) catalyst system of the invention is known in the art and is comprised of a carrier or support material having disposed thereon a non-volatile liquid film which contains rhodium in the form of rhodium metal, rhodium salts and/or rhodium complexes, the only proviso being that a rhodium complex should not contain ligands which insolubilize or poison the catalyst. Selection of the particular rhodium component may, in part, thus depend upon the solubility of the particular rhodium metal or compound in the specific non-volatile amorphous film which is utilized as the reaction medium. The rhodium compounds useful in the practice of the present invention include rhodium metal, rhodium oxides, $RhI_3$, $RhBr_3$, $RhCl_3$, $Rh(Acac)_3$, $Rh(CO)_2Acac$, $Rh_6(CO)_{16}$, $[RhCl(CO)_2]_2$ and $Rh(NO_3)_3$, wherein Acac represents acetylacetonate. Likewise, the rhodium useful in the practice of the present invention may be a rhodium carbonyl-phosphine complex which has been preformed. Illustrative examples of rhodium complexes include hydridocarbonyltris(triphenylphosphine) rhodium, rhodiumbis(triphenylphosphine) carbonylchloride and hydridobiscarbonylbis(triphenylphosphine) rhodium. Typical salt-like complexes include bis-ethyltricyclohexylphosphonium hexarhodiumpentadecylcarbonyl and bis(triphenylphosphine) rhodium carbonyl trifluoroacetate or perfluorobutyrate.

The concentration of the rhodium in the non-volatile amorphous film should be in the range from about 0.01 to 20 millimoles per gram of film. Preferably, the concentration of rhodium will be from about 0.5 to about 0.15 millimoles per gram of film.

The (SAPC) catalyst also contains a biphyllic ligand, i.e., a compound having at least one atom with a pair of electrons capable of forming a coordinate covalent bond with a rhodium atom and having the ability to accept an electron from the metal. Phosphines are the preferred ligands and have the general formula:

$PR_1R_2R_3$ wherein $R_1$, $R_2$ and $R_3$ are all independently selected from the group consisting of hydrogen, alkyl of 1 to 8 carbon atoms, aryl from 6 to 8 carbon atoms, and the amino, halo and alkoxy derivatives thereof. Preferably, $R_1$, $R_2$ and $R_3$ are all aryl groups containing from about 6 to about 8 carbon atoms. Aryl and mixed aryl/alkyl phosphines also may be used in the present invention. Sulfonated aryl derivatives are preferred in hydrophilic films. The most preferred phosphine is triphenylphosphine. Tricyclohexylphosphine, tri-iso-propylphosphine and tri-iso-butylphosphine also may be employed.

The amount of phosphine employed is not critical but, in general, it has been found that a molar ratio of rhodium to phosphine of about 4:1 is preferred. Broadly, a range of about 10:1 to about 1:10 is operable, however, typically, the molar ratio of rhodium to phosphine will be from about 10:1 to about 4:1.

In the present invention, a solid heterogeneous catalyst is used in the presence of a liquid phase catalyst which is supported thereon by means of a non-volatile amorphous film. Preparation of the catalyst is carried out by dissolving the rhodium catalyst in a low boiling volatile solvent such as chloroform, benzene, acetone, methanol, carbon tetrachloride, methanol, ethanol, and the like, which have a boiling point ranging from 10° C. to 120° C. (STP). A non-volatile liquid or polymer is also employed in conjunction with the volatile solvent for purposes of dispersing the rhodium catalyst and maintaining it in amorphous phase on the support material. The non-volatile amorphous film has a vapor pressure in the range of $10^{-12}$ mm to 10 mm Hg at 100° C., preferably $10^{-10}$ mm to 1 mm.

Representative non-volatile amorphous films, which remain liquid or above the polymer glass transition temperature under reaction conditions, include a wide variety of high boiling substituted and unsubstituted paraffin and aromatic hydrocarbons; organic esters, organic derivatives of nitrogen, sulfur, and phosphorus; organic derivatives of oxygen, e.g., propylene carbonate; high boiling derivatives of silicon; rubbery polymers (i.e., low glass transition temperature) high boiling inorganic or organic salts; eutectic melts, and the like. Volatile solvents and non-volatile solvents which act as films are described in U.S. Pat. No. 3,855,307, incorporated by reference. Polymers such as polybutadiene, polybutylmethacrylate, and the like, may be used providing their glass transition temperatures are below the reaction temperatures employed.

In preparing the (SAPC) catalyst according to the invention, the rhodium compound is dissolved in the non-volatile amorphous film and volatile solvent and the carrier or support material is added thereto. The resulting catalyst solution is thoroughly mixed and the volatile solvent is removed by volatization. The resulting catalyst, in powdered form, is then dried at temperatures of 20° C. to 40° C. under reduced pressure for a period of time ranging from 12 to 15 hours. The catalyst obtained thereby is a rhodium compound dispersed in the non-volatile liquid film which is supported on the carrier or support material.

An important embodiment of the (SAPC) catalyst composition is the use of excess biphyllic ligand as a component of the non-volatile amorphous film. Biphyllic ligands, such as the arylphosphines, e.g., triphenylphosphine, are generally used in rhodium complexes in amounts ranging from a stoichiometric equivalent to an excess up to about 25 weight percent, or more, based on the final catalyst. In the (SAPC) catalyst, however, the additional use of a triarylphosphine ligand as the non-volatile liquid film not only imparts stability to the rhodium complex but further serves to better disperse the rhodium compound. As shown in the examples hereinafter, a mixture of non-volatile amorphous films (polymer and liquid triphenylphosphine) were used in preparation of the (SAPC) catalyst composition, one of which employed a ten-fold excess of triphenylphosphine. While not being limited to theory, it is postulated that it is the use of excess ligand as a liquid film that provides excess phosphine in the amorphous film containing the catalyst leading to the unusually high selectivities to the normal aldehydes when the hydroformylation is carried out at mild temperatures at low pressures of 5 atmospheres or less.

Based on the weight of the carrier or support material, the amount of non-volatile liquid film employed will be in the range of about 1 wt. % to about 30 wt. %.

Suitable carrier or support materials include silica, silica-alumina, silica gel, alpha alumina, eta alumina, gamma alumina, aged or deactivated silica-alumina or silica-magnesia cracking catalysts, natural and acid treated clays, synthetic molecular sieves, such as zeolites X and Y, magnesia, magnesium silicate, diatomaceous earth, bauxite, titania, zirconia, cross-linked organic polymers, macroreticulated polymers, etc., which have a pore volume relative to solid weight of from 0.01 to 5.0 cm$^3$/gram of the carrier material. The size of the carrier or support material ranges from 375 mesh/inch to ⅛ inch particle size such that it can be employed in fixed or fluidized-bed reactors. In fluidized-bed operations, the carrier particles range in size from about 0.01 to 0.1 mm whereas in a fixed bed operation, the particle size ranges from 0.2 to 2.0 cm.

The surface area of the carrier or support material ranges from 1 to 1,200 square meters per gram and is preferably about 300 to 1,000 square meters per gram.

The degree of loading the SAPC catalyst ranges from 0.05 to 0.95 cm$^3$ of catalyst solution per cm$^3$ of pore volume of the carrier material, the catalyst solution containing the rhodium complex, the volatile solvent and the non-volatile liquid film. Loading of the rhodium complex on the carrier material will range between 0.1 wt. % and 5 wt. % (based on the rhodium metal content) with a preferred range being 0.2 wt. % to 3 wt. %. Generally, higher rhodium complex loadings achieve a faster reaction rate. A loading of between 0.2 and 0.8 cm$^3$ of catalyst solution per cm$^3$ of pore volume is generally preferred.

The following examples illustrate the best mode now contemplated for carrying out the invention.

EXAMPLE 1

25 ml of chloroform with 0.08 gm of propylene carbonate is added to a solid mixture containing 0.1 gm hydridocarbonyltris(triphenylphosphine)rhodium, $HRh(I)[(C_6H_5)_3P]_3CO$, 0.262 gm of triphenylphosphine and 0.6 gm of silica gel. After 2 minutes of stirring, the solvent is removed in a rotovap at room temperature. The yellow powder is dried in a vacuum oven overnight at 45° C. A 0.5 gm sample of this catalyst is placed in a stainless steel column of a flow reactor, placed in an oil bath at 80° C. and gas flow of 1:1:1 $H_2$/CO/propylene (15 psi, 9–14 ml/min) initiated. GC analysis of the products indicated a 0.8% conversion to aldehyde with a selectivity of 96%.

EXAMPLE 2

A 25 ml solution of chloroform and 0.06 gm polybutylmethacrylate (mol wt. 300,000) is added to a solid mixture containing 0.1 gm hydridocarbonyltris(triphenylphosphine)rhodium, $HRh(I)[(C_6H_5)_3P]_3(CO)$, 0.262 gm of triphenylphosphine and 0.60 gm of silica gel. After 2 minutes of stirring the solvent is removed in a rotovap at room temperature. The yellow powder is dried under vacuum overnight with the temperature not to exceed 45° C. A 0.50 gm sample of this product is placed in a stainless steel column of a gas flow reactor, placed in an oil bath at 80° C. and is subjected to a gas flow of 1:1:1 $H_2$/CO/propylene (15 psi, 9–14 ml/min). GC analysis of the products indicate the predominate production of n-butyraldehyde in conversions between 0.25 and 0.45% over a seven hour period (a nonintegratable peak where isobutyraldehyde should appear is observed). The selectivity of this procedure is greater than 99.5%.

EXAMPLE 3

The catalyst prepared in Example 2 is subjected 40 psi of a gas mixture containing 1:1:1 $H_2$/CO/propylene and the flow rate is maintained between 9 and 14 ml/min at 85° C.. The total conversion reached 2.09% with 98.8% selectivity for n-butyraldehyde.

EXAMPLE 4

A 25 ml solution of chloroform and 0.057 gm silicone gum rubber is added to a solid mixture containing 0.1 gm hydridocarbonyltris(triphenylphosphine)rhodium, $HRh(I)[(C_6H_5)_3P]_3(CO)$, 0.262 gm of triphenylphosphine and 0.60 gm of silica gel. After 2 minutes of stirring the solvent is removed in a rotovap at room temperature. The yellow powder is dried under vacuum overnight with the temperature not to exceed 45° C. A 0.50 gm sample of this product is placed in a stainless steel column of a gas flow reactor, placed in an oil bath at 75° C. and is subjected to a gas flow of 1:1:1 H2/CO/propylene (15 psi, 9–14 ml/min). GC analysis of the products indicates a 2.5% overall conversion to normal and isobutyraldehyde and 92.2% selectivity to n-butyraldehyde.

EXAMPLE 5

A 25 ml solution of chloroform and 0.08 gm propylene carbonate is added to a solid mixture containing 0.1 gm hydridocarbonyltris(triphenylphosphine)rhodium, $HRh(I)[P(C_6H_5)]_3(CO)$, 0.262 gm of triphenylphosphine and 0.60 gm of silica gel. After 2 minutes of stirring the solvent is removed in a rotovap at room temperature. The yellow powder is dried under vacuum overnight with the temperature not to exceed 45° C. A 0.50 gm sample of this product is placed in a stainless steel column of a gas flow reactor, placed in an oil bath at 80° C. and is subjected to a gas flow of 1:1:1 $H_2/CO$/propylene (15 psi, 9-14 ml/min). GC analysis of the products indicates the exclusive production (99.99%) of n-butyraldehyde in 0.5% conversions over a one hour period. When the reaction temperature is increased to 100° C. the conversions to n-butyraldehyde increase to 2.7% and the production of isobutyraldehyde is evident (the selectivity of n-butyraldehyde to isobutyraldehyde drops to 97.5%). Increasing the temperature to 100° C. and the pressure to 60 psi results in an increase of conversions to 2.8% but a decrease in selectivity to 89%.

EXAMPLE 6

The catalyst prepared in Example 2 is subjected to 15 psi of a gas mixture containing 1:1:1 $H_2/CO$/propylene and the flow rate is maintained between 9 and 14 ml/min at 90° C. for one hour. The conversion to n-butyraldehyde reached 1.9% with 91.6% selectivity. Increasing the gas pressure to 60 psi, the conversion to n-butyraldehyde increases to 3.7% and the selectivity is 97%. Decreasing the temperature to 80° C. and keeping a 60 psi gas pressure resulted in conversions of 2.1% and 95.6% selectivity.

EXAMPLE 7

A 25 ml solution of chloroform and 0.06 gm polybutylmethacrylate (mol wt. 300,000) is added to a solid mixture containing 0.1 gm hydridocarbonyltris(triphenylphosphine)rhodium, $HRh(I)[P(C_6H_5)]_3(CO)$ and 0.60 gm of silica gel (no triphenylphosphine was added). After 2 minutes of stirring the solvent is removed in a rotovap at room temperature. The yellow powder is dried under vacuum overnight with the temperature not to exceed 45° C. A 0.50 gm sample of this product is placed in a stainless steel column of a gas flow of 1:1:1 $H_2/CO$/propylene (15 psi, 9-14 ml/min). GC analysis of the products indicate a 0.34% conversion to n-butyraldehyde and a 0.13% conversion to isobutyraldehyde yielding only 72.4% selectivity.

EXAMPLE 8

The catalyst prepared in Example 4 is subjected 60 psi of a gas mixture containing 1:1:1 $H_2/CO$/propylene and the flow rate is maintained between 9 and 14 ml/min at 80° C. After one hour GC analysis showed a 1.3% conversion to n-butyraldehyde with 97% selectivity. When the pressure is increased to 80 psi, the conversions are 1.4% with a 96% selectivity.

EXAMPLE 9

A 25 ml solution of chloroform and 0.06 gm polybutylmethacrylate (mol wt. 300,000) is added to a solid mixture containing 0.1 gm hydridocarbonyltris(triphenylphosphine)rhodium, $HRh(I)[P(C_6H_5)]_3(CO)$, 0.262 gm of triphenylphosphine and 0.60 gm of silica gel. After 2 minutes of stirring the solvent is removed in a rotovap at room temperature. The yellow powder is dried under vacuum overnight with the temperature not to exceed 45° C. A 0.50 gm sample of this product is placed in a stainless steel column of a gas flow reactor, placed in an oil bath at 80° C. and is subjected to a gas flow of 1:1:0.1 $H_2/CO$/propylene (15 psi, 9-14 ml/min). GC analysis of the products indicate a maximum conversion to n-butyraldehyde of 22.3% within the first ten minutes. The selectivity for this process is 74.5%. Increasing the pressure to 60 psi gives a maximum conversion of 30% after one hour.

EXAMPLE 10

A 25 ml solution of chloroform and 0.08 gm propylene carbonate is added to a solid mixture containing 0.1 gm hydridocarbonyltris(triphenylphosphine)rhodium, $HRh(I)[P(C_6H_5)]_3(CO)$, 0.262 gm of triphenylphosphine and 0.60 gm of silica gel. After 2 minutes of stirring the solvent is removed in a rotovap at room temperature. The yellow powder is dried under vacuum overnight with the temperature not to exceed 45° C. A 0.50 gm sample of this product is placed in a stainless steel column of a gas flow reactor, placed in an oil bath at 80° C. and is subjected to a gas flow of 1:1:0.1 $H_2/CO$/propylene (15 psi, 9-14 ml/min). GC analysis of the products indicate the predominate production of n-butyraldehyde in conversions reaching a maximum of 6.2% after 30 minutes. The selectivity of this procedure is greater than 98.5%.

EXAMPLE 11

A 25 ml solution of methylene chloride and 0.60 gm chrome supported on a liquid phase of diethyleneglycol succinate (15% solution)* was added to a solid mixture containing 0.1 gm hydridocarbonyltris(triphenylphosphine)rhodium, $HRh(I)[P(C_6H_5)]_3(CO)$ and 0.262 gm of triphenylphosphine. After 2 minutes of stirring the solvent is removed in a rotovap at room temperature. The yellow powder is dried under vacuum overnight with the temperature not to exceed 45° C. A 0.50 gm sample of this product is placed in a stainless steel column of a gas flow reactor, placed in an oil bath at 80° C. and is subjected to a gas flow of 1:1:1 $H_2/CO$/propylene (15 psi, 9-14 ml/min). GC analysis of the products indicates the exclusive production of n-butyraldehyde with conversions approaching 0.5% over a one hour period yielding 99.99% selectivity.

* Chrome W AW, registered trademark

EXAMPLE 12

A 25 ml solution of chloroform and 0.09 gm diethylene phthalate is added to a solid mixture containing 0.1 gm hydridocarbonyltris(triphenylphosphine)rhodium, $HRh(I)[P(C_6H_5)]_3(CO)$, 0.26 gm triphenylphosphine and 0.60 gm of silica gel. After 2 minutes of stirring the solvent is removed in a rotovap at room temperature. The yellow powder is dried under vacuum overnight with the temperature not to exceed 45° C. A 0.50 gm sample of this product is placed in a stainless steel column of a gas flow reactor, placed in an oil bath at 80° C. and is subjected to a gas flow of 1:1:1 $H_2/CO$/propylene (15 psi, 9-14 ml/min). GC analysis of the products indicate a 4.69% conversion to n-butyraldehyde and a 0.08% conversion to isobutyraldehyde yielding 98.3% selectivity.

EXAMPLE 13

A 25 ml solution of chloroform and 0.09 gm tri-N-butyl phosphate is added to a solid mixture containing 0.1 gm hydridocarbonyltris(triphenylphosphine)rhodium, $HRh(I)[P(C_6H_5)]_3(CO)$, 0.262 gm of triphenylphosphine and 0.60 gm of silica gel. After 2 minutes of stirring the solvent is removed in a rotovap at room temperature. The yellow powder is dried under vacuum overnight with the temperature not to exceed 45° C. A 0.50 gm sample of this product is placed in a stainless steel column of a gas flow reactor, placed in an oil bath at 80° C. and is subjected to a gas flow of 1:1:0.1

$H_2$/CO/propylene (15 psi, 9–14 ml/min). GC analysis of the products indicate a conversion to n-butyraldehyde approaching 1.8% for a one hour period. The selectivity for this process is 73%.

EXAMPLE 14

A 25 ml solution of chloroform and 0.6 gm of a substituted quaternary alkyl ammonium salt (trioctylmethyl ammonium chloride; trademane Aliquot 336) is added to a solid mixture containing 0.1 gm hydridocarbonyltris(triphenylphosphine)rhodium, $HRh(I)[P(C_6H_5)]_3(CO)$, 0.262 gm of triphenylphosphine and 0.60 gm of silica gel. After 2 minutes of stirring the solvent is removed in a rotovap at room temperature. The yellow powder is dried under vacuum overnight with the temperature not to exceed 45° C. A 0.50 gm sample of this product is placed in a stainless steel column of a gas flow reactor, placed in an oil bath at 80° C. and is subjected to a gas flow of 1:1:0.1 $H_2$/CO/propylene (15 psi, 9–14 ml/min). GC analysis of the products indicate the exclusive production of n-butyraldehyde with conversions of 1 to 1.2% over a seventy minute run, yielding a selectivity of 99.99%.

EXAMPLE 15

A 25 ml solution of chloroform and 0.06 gm polybutadiene (mol wt. 300,000) is added to a solid mixture containing 0.1 gm hydridocarbonyltris(triphenylphosphine)rhodium, $HRh(I)[P(C_6H_5)]_3(CO)$, 0.262 gm of triphenylphosphine and 0.60 gm of silica gel. After 2 minutes of stirring the solvent is removed in a rotovap at room temperature. The yellow powder is dried under vacuum overnight with the temperature not to exceed 45° C. A 0.50 gm sample of this product is placed in a stainless steel column of a gas flow reactor, placed in an oil bath at 80° C. and is subjected to a gas flow of 1:1:1 $H_2$/CO/propylene (15 psi, 9–14 ml/min.). GC analysis of the products indicate a 3.3% conversion to $C_4$ aldehydes with 94.5% selectivity to n-butyraldehyde over a two-hour period.

EXAMPLE 16

A 75 ml solution of chloroform and 0.11 gm polybutadiene (mol wt. 300,000) is added to a solid mixture containing 0.45 gm hydridocarbonyltris(triphenylphosphine)rhodium, $HRh(I)[P(C_6H_5)]_3(CO)$, 1.31 gm of triphenylphosphine and 3.00 gm of silica gel. After 2 minutes of stirring the solvent is removed in a rotovap at room temperature. The yellow powder is dried under vacuum overnight with the temperature not to exceed 45° C. A 0.50 gm sample of this product is placed in a stainless steel column of a gas flow reactor, placed in an oil bath at 100° C. and is subjected to a gas flow of 1:1:1 $H_2$/CO/propylene (15 psi, 9–14 ml/min.). GC analysis of the products indicate a 1.3% conversion to $C_4$ aldehydes with greater than 99.5% selectivity to n-butyraldehyde over a two-hour period.

EXAMPLE 17

The catalyst prepared in Example 16 is subjected to 15 psi of a gas mixture containing 1:1:2 $H_2$/CO/propylene and the flow rate is maintained between 9 and 14 ml/min at 100° C. The total conversion reached 1.34% with greater than 99.5% selectivity for n-butyraldehyde.

EXAMPLE 18

25 ml of chloroform and polyethylene glycol (0.2 g, MW 8,000) was added to a solid mixture containing $HRh(I)[(C_6H_5)]_3(CO)$ (0.1 g, of triphenylphosphine (0.83 g) and silica gel (0.6 g). After 2 minutes of stirring, the solvent was removed by evaporation at room temperature. The yellow powder is dried under vacuum overnight at room temperature. The catalyst (0.10 g), 1-hexene (10 ml) and 2-octanone (0.1 ml) were placed in a glass tube, pressurized to 40 psig with syn gas (1:1 $H_2$/CO) and set in an oil bath at 75° C. Gas Chromatographic analysis after 90 minutes indicates the production of n-heptanal, 61 TON, and 2-methyl hexanal, 22 TON. A TON is defined as a turnover number and is the moles of product divided by the moles of catalytic complex, in this case $Hrh(I)[(C_6H_6)]_3(CO)$. The selectivity of this system is 2.7:1 favoring heptanal.

EXAMPLE 19

Water (25 ml) and poly(ethylene glycol) (0.2 g, MW 8,000) are added to a solid mixture containing $HRh(I)[P(C_6H_4SO_3Na)_3]_3(CO)$ (0.184 g), $P[(C_6H_4SO_3Na)_3]_3$ (0.127 g) and of silica gel (0.6 g). After 2 minutes of stirring, the solvent is removed by evaporation at room temperature. The catalyst (0.10 g), 1-hexene (10 ml), water (0.5 ml) and 2-octanone (0.1 ml) were placed in a glass tube, pressurized to 50 psig with syn gas (1:1 $H_2$/CO) and set in an oil bath at 85° C. Gas chromatographic analysis after 1 hour indicates the production of n-heptanal. After 4 hours, twenty-seven turnovers occurred. The production of 2-methyl hexanal is not observed.

What is claimed is:

1. In the hydroformylation of olefins having 2 to 6 carbon atoms to produce normal aldehydes which comprises contacting a gaseous mixture of said olefin, carbon monoxide and hydrogen in vapor phase with a supported liquid phase heterogeneous catalyst comprising a carrier having disposed thereon a non-volatile liquid film containing a rhodium complex, the improvement which comprises contacting said olefin at temperatures of 80° C. to 100° C. under a gas pressure of 1 to 5 atmospheres to obtain a product selectivity to normal aldehyde product of at least 95%.

2. The method of claim 1 wherein the rhodium complex is hydridocarbonyltris(triphenylphosphine) rhodium and the non-volatile liquid film is a triarylphosphine.

3. The method of claim 2 wherein the triarylphosphine is triphenylphosphine.

4. The method of claim 2 wherein the carrier is selected from the group consisting of silica, alumina and mixtures thereof.

5. The method of claim 3 or 4 wherein the gas pressure is 1 to 3 atmospheres.

6. The hydroformylation of propylene to produce normal butyraldehyde which comprises contacting a gaseous mixture of propylene, carbon monoxide and hydrogen in vapor phase with a supported liquid phase heterogeneous catalyst comprising a carrier having disposed thereon a non-volatile liquid film containing a rhodium complex, said contacting of propylene being carried out at temperatures of 80° C. to 100° C. atmospheres to obtain a product selectivity to normal butyraldehyde of at least 95%.

7. The method of claim 6 wherein the non-volatile liquid film comprises triarylphosphine in combination with a second non-volatile liquid film having a vapor pressure in the range of $10^{-12}$ mm to 10 mm Hg at 100° C.

8. The method of claim 7 wherein the second non-volatile liquid film is selected from the group consisting of propylene carbonate, polybutylmethacrylate, silicon gum rubber, diethyleneglycol succinate, diethyl phthalate, tri-N-butylphosphate polybutadiene and an alkyl ammonium salt.

9. The method of claim 8 wherein the rhodium complex is hydridocarbonyltris(triphenylphosphine) rhodium and the non-volatile liquid film is a triarylphosphine.

10. The method of claim 8 wherein the triarylphosphine is triphenylphosphine.

11. The method of claim 8 wherein the carrier is selected from the group consisting of silica, alumina and mixtures thereof.

12. The method of claim 8 wherein the gas pressure is 1 to 3 atmospheres.

* * * * *